US006625897B2

United States Patent
Tadin

(10) Patent No.: US 6,625,897 B2
(45) Date of Patent: *Sep. 30, 2003

(54) METHOD AND APPARATUS FOR MEASURING FOOT GEOMETRY

(75) Inventor: Tony G. Tadin, Woodside, CA (US)

(73) Assignee: Amfit, Inc., Santo Clara, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 09/840,489

(22) Filed: Apr. 23, 2001

(65) Prior Publication Data

US 2002/0046472 A1 Apr. 25, 2002

Related U.S. Application Data

(63) Continuation-in-part of application No. 09/692,015, filed on Oct. 18, 2000, now Pat. No. 6,493,958.

(51) Int. Cl.[7] ............................................... A61B 5/103
(52) U.S. Cl. ........................................ 33/515; 33/514.2
(58) Field of Search ............................... 33/515, 514.2, 33/1 BB, 512; 12/1 G, 21

(56) References Cited

U.S. PATENT DOCUMENTS

| | | | | |
|---|---|---|---|---|
| 2,330,317 A | * | 9/1943 | Stewart | 33/515 |
| 2,472,754 A | * | 6/1949 | Mead | 33/515 |
| 4,876,758 A | | 10/1989 | Rolloff et al. | 12/142 N |
| 4,998,354 A | * | 3/1991 | Silverman et al. | 33/514.2 |
| 5,390,680 A | * | 2/1995 | Brenner | 33/515 |

* cited by examiner

Primary Examiner—Christopher W. Fulton
(74) Attorney, Agent, or Firm—Ohlandt, Greeley, Ruggiero & Perle, L.L.P.

(57) ABSTRACT

An apparatus for measuring a plantar contour of a foot of a user, the plantar contour having a height. The apparatus comprises an impression block having a thickness sufficient to form an impression of at least a portion of the height of the plantar contour. A method for forming an insole corresponding to a plantar contour of a foot of a user, wherein the plantar contour has a height. The method comprises the steps of (1) placing the foot of the user into an impression block having a thickness wherein the thickness is sufficient to form an impression of at least a portion of the height of the plantar contour (i.e., a portion or the full arch contour); (2) forming a digitized model of the impression; (3) extrapolating data from the digitized model of the impression to form a complete digitized model of the full height of the plantar contour; (4) providing the complete digitized model to a milling machine; and (5) directing the milling machine to manufacture the insole using the complete digitized model.

27 Claims, 26 Drawing Sheets

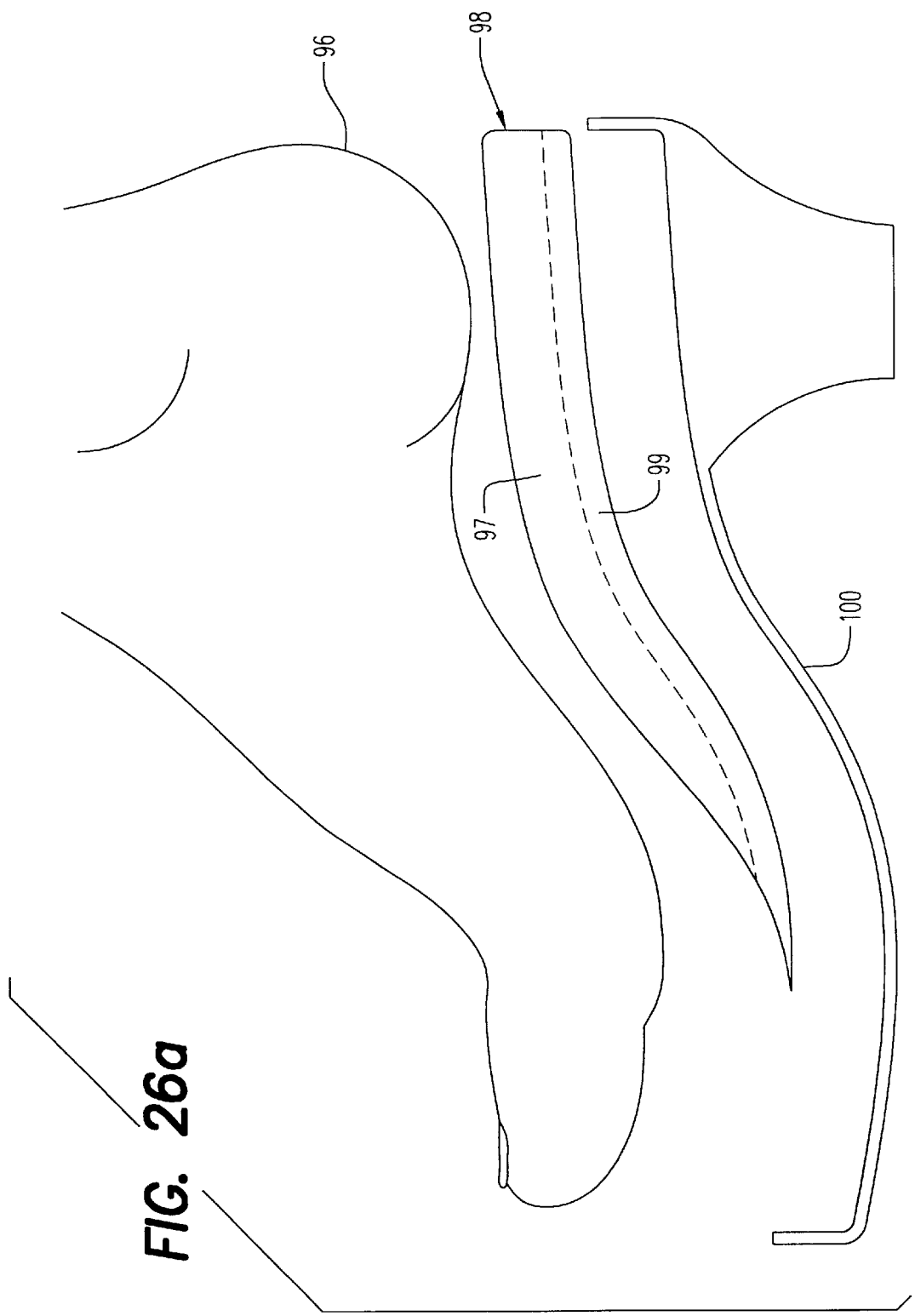

METHOD AND APPARATUS FOR MEASURING FOOT GEOMETRY

This application is a Continuation-in-part application of U.S. application Ser. No. 09/692,015, filed on Oct. 18, 2000, now U.S. Pat. No. 6,493,958, the disclosure of which is incorporated in its entirety herein by reference.

BACKGROUND OF THE INVENTION

1. Field of the Invention

The present invention relates to an apparatus for measuring the geometry of a person's plantar contour and a method of forming a custom insole corresponding to the measured plantar contour. More particularly, the present invention relates to an impression block for taking a partial measurement of the plantar contour that can be extrapolated to produce a custom insole.

2. Description of the Related Art

A number of methods currently exist to measure the geometry of the plantar contour of a foot. The accurate measurement of the plantar contour is used in the manufacture of custom insoles. The prior art methods include plaster casting, optical scanning, contact sensor measurement, as well as impression measurement. These methods prefer the foot to be in a neutral position. However, some shoes, such as high heels or other shoes with a slope, distort the plantar contour and instep due to the shifting of the user's body weight. Accordingly, the insoles made using these prior art methods do not account for such distortions. Moreover, these prior art methods are not well suited for home use.

The optical scanning methods and contact sensor measurement methods utilize expensive equipment. These methods provide an accurate and complete measurement of the foot. But, the size, expense and complexity of the equipment necessary for these methods makes them not suitable for use in all locations. Moreover, these methods do not permit accurate measurement of the geometry of the foot in the position it will be in when inside of a shoe.

Plaster casting methods require the measurement to be performed by a person other then the one being measured. This method provides an accurate and complete measurement of the foot but can be very messy and time consuming. Thus, plaster casting methods are not suitable for use in a person's home or by one's self. Moreover, these methods do not permit accurate measurement of the geometry of the foot in the position it will be in when inside of a shoe.

Impression measurement methods and apparatus utilize an easily deformable block. A person steps onto the block, thus crushing the block in the locations of higher pressure. In this manner, the block deforms in the approximate shape of the persons' plantar contour. While this prior art method may be suitable for home use, it produces a sub-optimal characterization of the foot for a number of reasons. First, the block is uniform in thickness from heel to toe. This causes the toes to be forced upward as the foot is pressed into the block because the toes of the foot have substantially less pressure on them than the region of the foot from the heel to the metatarsal heads. Forcing the toes upward can cause a number of problems including, hyperextension of the plantar fascia, lowering of the correct arch height, and improper measurement of the forefoot and heel. Second, under full body weight, the foot expands allowing for a larger than normal foot impression. Additionally, the prior art does not provide for measurement of the instep. Moreover, the current materials and methods do not permit accurate measurement of the geometry of the foot in the position it will be in when inside of a shoe.

In the manufacture of custom insoles, the use of the plaster casting and impression methods also require the use of a scanning system. The scanning system may act directly on the negative impression within the block or plaster. Scanning systems that act directly on negative impressions are known in the art. These laser-scanning systems consist of a laser with a line generating optic. The laser projects a line at a known incident angle onto the negative impression. A camera is used to read the position of the laser line on the negative impression. Alternatively, the scanning system may act upon a positive model using a casting medium such as plaster, wax or equivalent made form a negative impression contained in the foam block. One such scanning system, provided by U.S. Pat. No. 4,876,758, specially constructed array of pin-like sensors. In either circumstance, the scanning system is used to digitize the measured contour. The digitized contour is provided to a computer controlled milling machine. The milling machine uses the digitized information to manufacture a custom insole matching the digitized contour. Accordingly, the apparatus and methods of the present invention provide for cheaper, improved and easier means to provide custom manufactured insoles to a customer.

Previously, the prior art impression block is required to measure the entire plantar contour in order for the scanning system to create a digitize contour sufficient to manufacture the custom insole. More specifically, the prior art impression block requires a thickness equal to or greater than the thickness of the blank used to manufacture the custom insole. However, impression blocks of such thickness have many drawbacks, such as large shelf space requirements, increased packaging costs, and increased shipping costs. In the instance where the prior art impression block is directed for use at home by the user and then to be shipped to a location for manufacture of the insole, such thick prior art devices are simply not practical.

Accordingly, the present invention provides foot measurement apparatus and methods, which overcome the limitations set forth above.

SUMMARY OF THE INVENTION

The present invention provides an apparatus for measuring a plantar contour of a foot of a user. The apparatus comprises a carrier and an impression block in the carrier. The impression block has a guide formed therein to aid the user in aligning the foot with respect to the impression block.

The present invention also provides an apparatus for measuring a plantar contour of a foot of a user where the plantar contour has a height. The apparatus comprises an impression block having a thickness sufficient to form an impression of at least a portion of the height of the plantar contour.

Additionally, the present invention provides a method for forming a complete digitized model of the height of a plantar contour of a foot of a user, wherein the plantar contour has a height. The method comprises the steps of: (1) placing the foot of the user into an impression block having a thickness, wherein the thickness is sufficient to form an impression of at least a portion of the height of the plantar contour; (2) forming a digitized model of the impression; (3) extrapolating data from the digitized model of the impression to form the complete digitized model of the full height of the plantar contour; and (4) forming a digitized model of the portion of the plantar contour; and (5) fabricating an insole from the portion of the digitized contour.

An additional embodiment according to the present invention comprising an apparatus for measuring a plantar contour of a foot of a user having at least a portion of a shoe and an impression block disposed within the shoe, wherein the impression block has a guide formed therein to aid the user in aligning the foot with respect to the impression block. Preferably, the impression block includes a first layer and a second layer, wherein the first layer is of lesser density than the second layer. Alternatively, the impression block is contained within a compliant Still an additional embodiment includes a method for forming a complete digitized model of the height of a plantar contour of a foot of a user, wherein the plantar contour has a height. The method comprises: placing the foot of the user into an impression block having a thickness and wherein a compliant medium is disposed between the impression block and the foot, wherein the thickness is sufficient to form an impression of at least a portion of the height of the plantar contour; filling the impression with a material which is capable of making a mold of the impression; forming a digitized model of the mold; and extrapolating data from the digitized model of the mold to form either a complete or partial digitized model of the full or partial height of the plantar contour, respectively.

BRIEF DESCRIPTION OF THE DRAWINGS

FIG. 9b is a side view of the die cut blank of FIG. 9a.

FIG. 20b is a side view of the dual density embodiment of FIG. 20a.

FIG. 26a is an exploded side view of a foot, a shorter three quarters sized dual density foam impression cartridge and a partial women's heeled shoe.

DESCRIPTION OF THE PREFERRED EMBODIMENT

Figure 1:
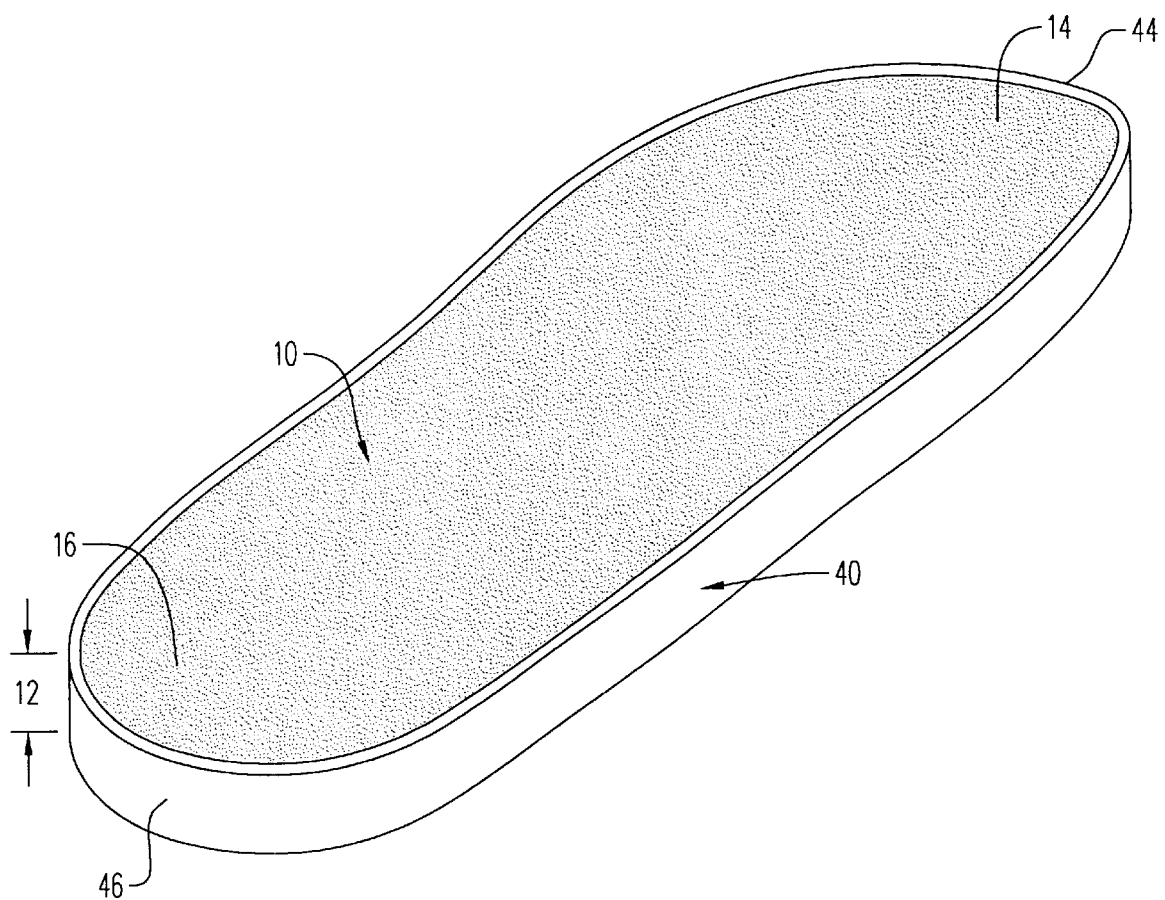
FIG. 1 is a rear perspective view of the impression block of the present invention.

Referring to the figures and more particularly to FIG. 1, an impression block 10 of the present invention is shown. Block 10 is made from pressure sensitive materials, which compress when a person's foot is pressed into the block. Preferably, block 10 comprises a casting material having low density, high flexural modulus and low shear strength. Accordingly, block 10 provides a material, which is easily deformed, with little or no memory, and retains the deformed shape indefinitely. Expanded phenolic materials such as those commonly used for insulation and ultra low density expanded polystyrene are suitable for block 10. In the preferred embodiment, block 10 is expanded phenolic material.

Preferably, block 10 has a hardness or density from about 0.5 to about 25 pounds per square inch (hereinafter "psi"). Selection of the correct block 10 density depends on factors such as body weight, lifestyle or desired usage (e.g., sport, casual, or formal). For example, a soft density is a density from about 0.5 to 5 psi, preferably 2 to 3 psi. Such soft density blocks 10 are selected for casting a foot in block 10 while in the sitting position. A medium density is a density from about 5 to 10 psi and is selected for casting a foot in block 10 while in standing position. A hard, weight bearing density is a density from about 5 to 25 psi, preferably 8 to 15 psi. Such hard density blocks 10 are selected for taking a dynamic casting of a foot in block 10.

Shown in FIG. 1, block 10 has a thickness 12, a front or toe receiving end 14 and a rear or heel-receiving end 16. Importantly, thickness 12 is sufficient to form an impression of at least a portion of the overall height of the user's plantar contour. In a first embodiment, thickness 12 is equal to less than half of the height of the plantar contour. In another embodiment, thickness 12 is equal to less than one third of the height of the plantar contour. More specifically, thickness 12 is in a range from about 8 mm to about 15 mm. In a preferred embodiment, thickness 12 of front end 14 is substantially identical to the thickness of rear end 16. In alternate embodiments, thickness 12 of front end 14 is less than the thickness of rear end 16.

Accordingly, block 10 of the present invention is adapted to form at least a partial measurement of the user's plantar contour. As described herein by example, block 10 is adapted to form at least a partial measurement of the user's entire plantar contour. However, it is considered within the scope of the present invention for block 10 to be adapted to form at least a partial measurement of the only specific portion of user's plantar contour, such as, but not limited to, heel, arch and the like.

As discussed above, a scanning system is used to digitize the measured contour. The digitized contour is provided to a computer controlled milling machine. The milling machine uses the digitized information to manufacturing a custom insole matching the digitized contour from an insole blank. The inventors have found that a complete plantar contour can be extrapolated from the partial measurement of the user's entire plantar contour.

Preferably, block 10 is disposed in carrier or container 40. Carrier 40 includes a front or toes receiving end 44 and a rear or heel-receiving end 46. Block 10 is disposed in carrier 40 such that rear end 16 of the block is adjacent rear end 46 of the carrier and front end 14 of the block is adjacent front end 44 of the carrier.

Figure 2:
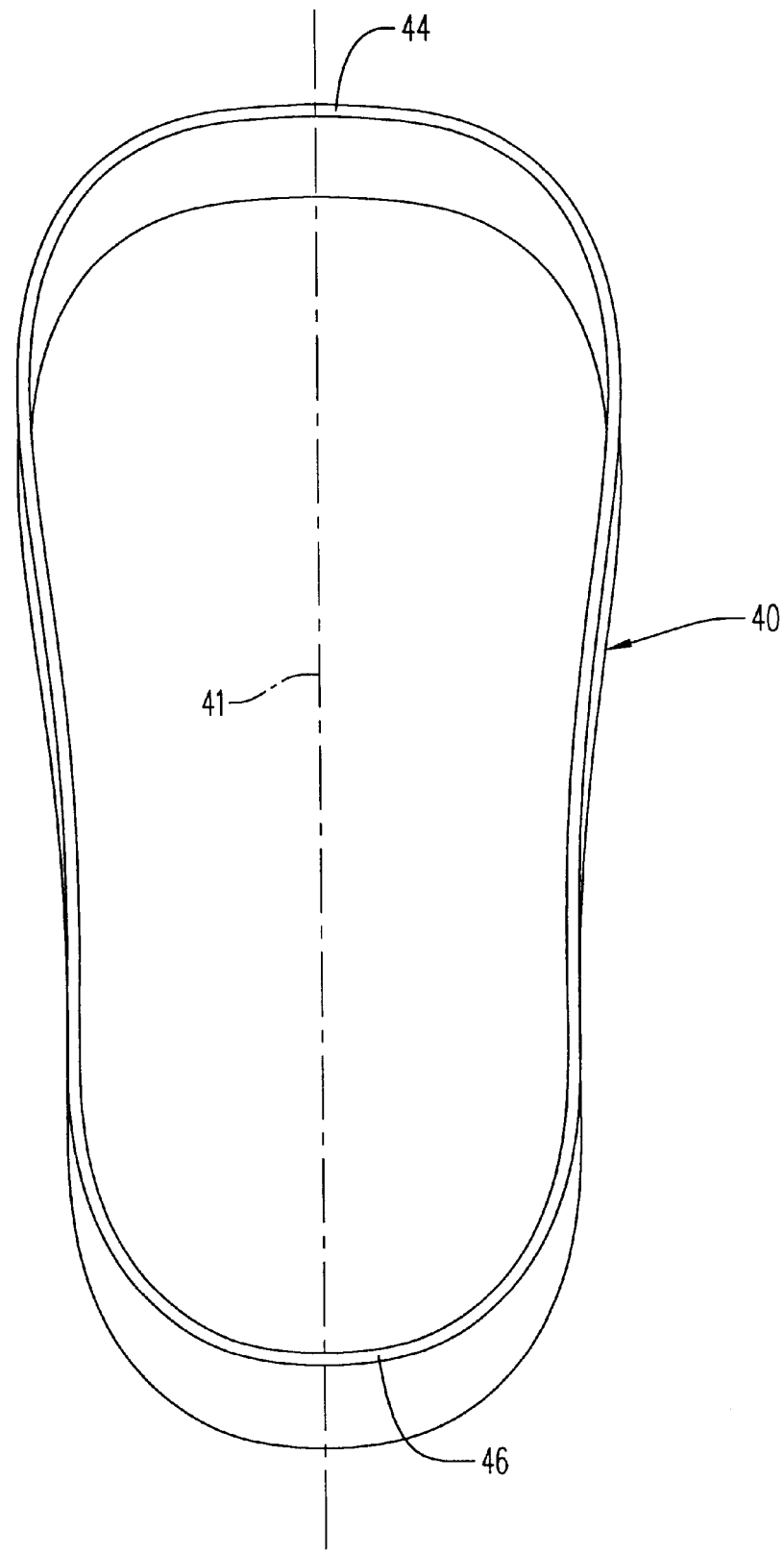
FIG. 2 is a rear perspective view of an embodiment of the container of the present invention.

Carrier 40 is adapted for use as for taking an impression of either a left foot or a right foot. Preferably, carrier 40 shown in FIG. 2 is symmetrical about its longitudinal axis 41. Thus, carrier 40 provides for sufficient surface area in both front end 44 and rear end 46 so as to allow the carrier to be used for either foot. Accordingly, carrier 40 reduces manufacturing costs by enabling a single mold to be used to manufacture the carrier and by eliminating the need to carry specific right foot carriers and left foot carriers in inventory.

Figure 3:
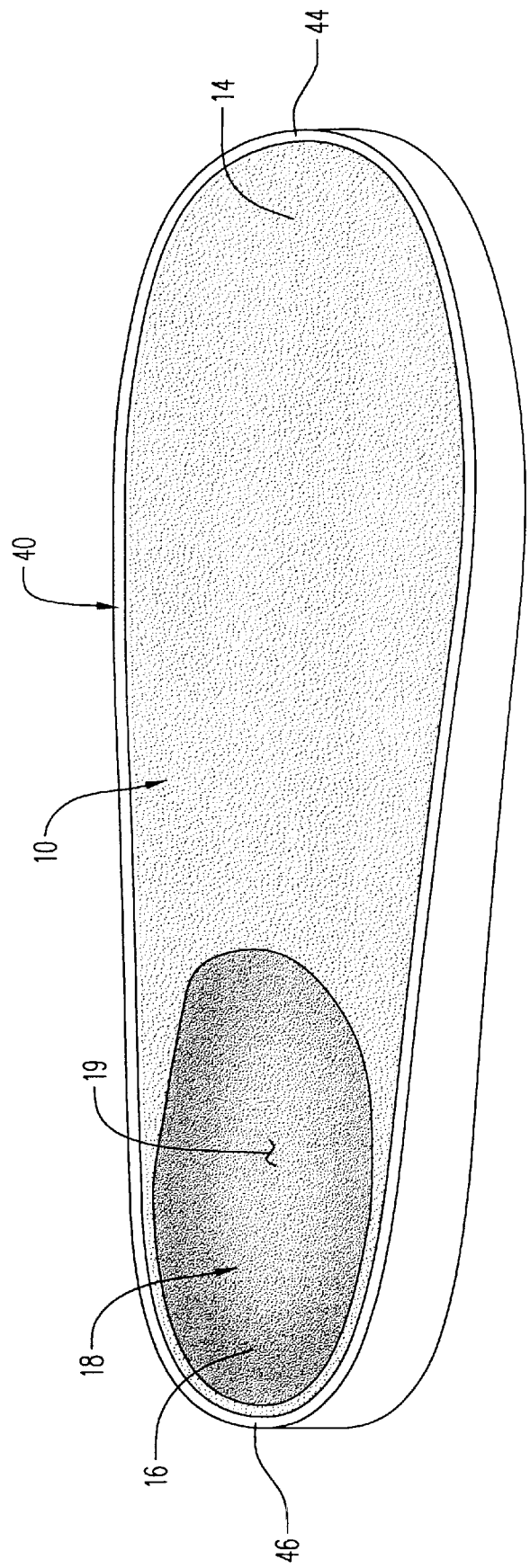
FIG. 3 is a side perspective view of an embodiment of the guide of the present invention.

In an alternate embodiment, block 10 includes a guide 18 to ensure the user properly aligns the foot in the block. Guide 18, shown in FIG. 3, is an indentation 19 formed within block 10. Accordingly, guide 18 forms a natural locator for the user to place at least a portion of their foot into in order to align their foot in block 10. Preferably, indentation 18 is adjacent rear end 16 of the block and is of sufficient depth to allow the user to align their heel with block 10. In an alternate embodiment, indentation 18 is adjacent front end 16 of the block and is of sufficient depth to allow the user to align their toes with block 10.

Figure 4:
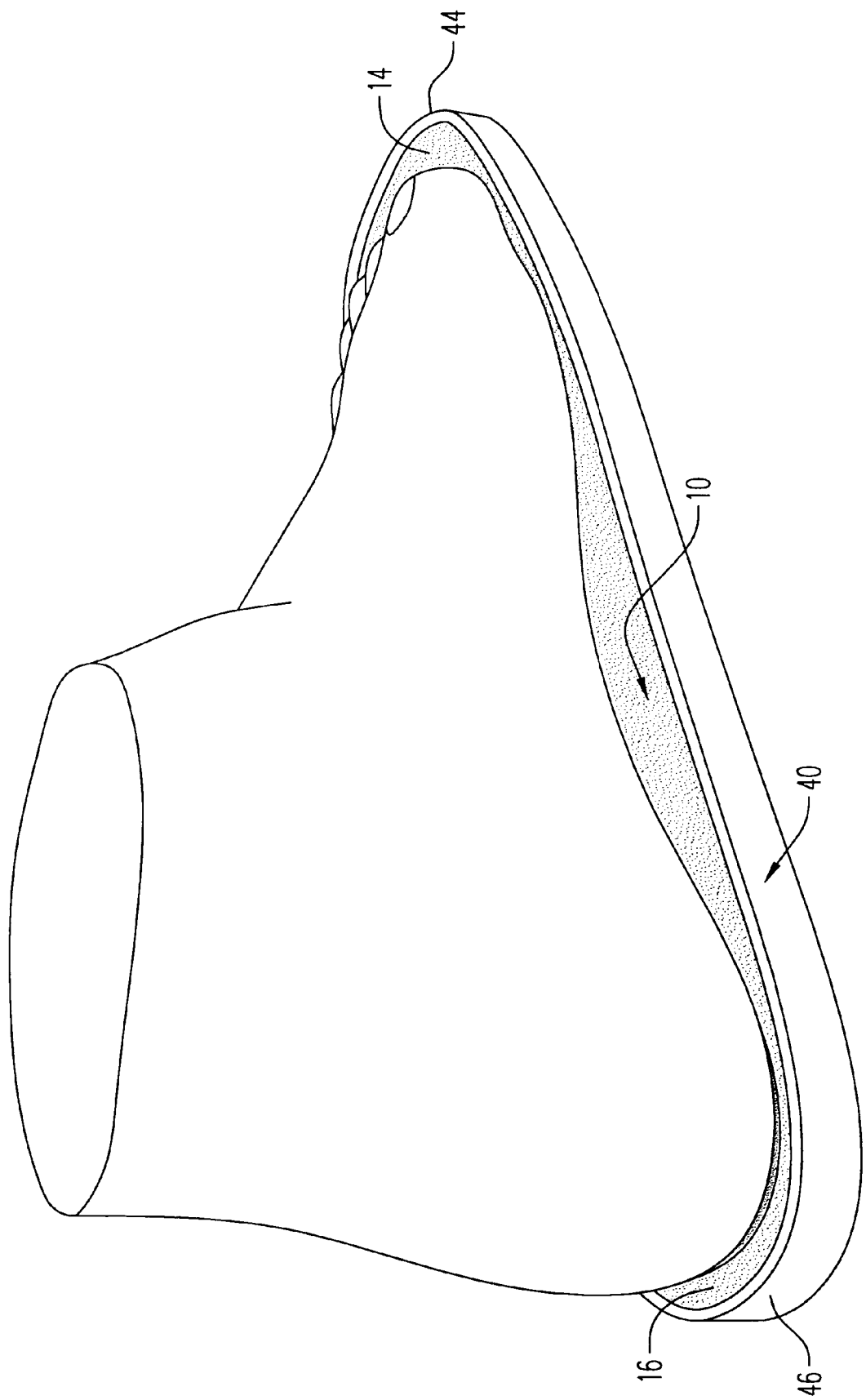
FIG. 4 is a rear perspective view of the impression block of FIG. 1 taking an impression.
Figure 5:
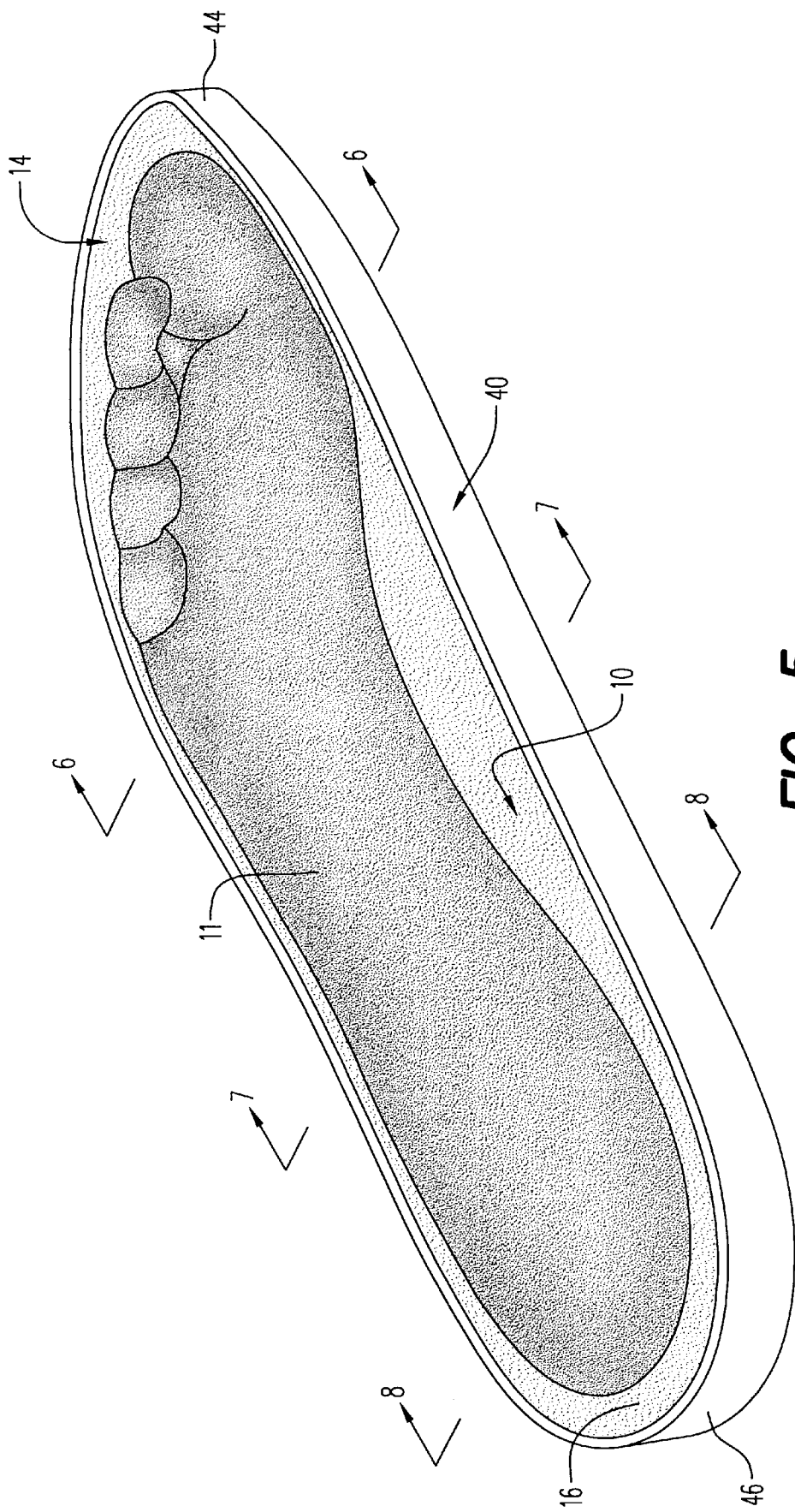
FIG. 5 is a rear perspective view of the impression block of FIG. 1 after taking an impression.

By way of example, the use of block 10 to measure a person's plantar contour is described below with reference to the embodiment of block 10 shown in FIG. 1. The user positions one foot over block 10 with their toes toward front portion 14 and their heel towards rear portion 16 and moves their foot into the block as shown in FIG. 4. Next, the user applies weight to the foot on block 10 until the block is deformed to form a negative impression of at least a partial plantar contour 11. Next, the user removes that foot from block 10 leaving the impression of the partial plantar contour 11 as shown in FIG. 5.

As described above, impression of the partial plantar contour 11 formed in block 10 is used in the manufacture of custom insoles. The process of converting impression of the partial plantar contour 11 into the custom insole often times requires using a scanner to digitize the contour directly from the impression or by forming a positive model from the impression. By way of example the present invention is described using a scan taken directly from impression of the partial plantar contour 11. However, it is considered within the scope of the present invention to include scanning from a positive model made from the impression.

Partial plantar contour 11 is extrapolated to form a complete plantar contour 11'. Complete plantar contour 11' is provided to a computer controlled milling machine. The milling machine uses complete plantar contour 11' to manufacturing the custom insole from an insole blank. However, when desirable the partial plantar contour is all that is required for low profile insole supports.

The scanning system forms a digitized model of partial plantar contour 11. Periodic cross sections of partial plantar contour 11 are then generated. For example, a plurality of cross sections 15 shown in FIGS. 6 through 8 formed along lines 6—6 through 8—8 of FIG. 5 are generated. A sufficient number of cross-sections 15 to extrapolate complete plantar contour 11' are formed. In the preferred embodiment, cross-sections 15 are generated in intervals of about 2 mm. However, for purposes of clarity only three cross sections 15 are described.

Figure 6:
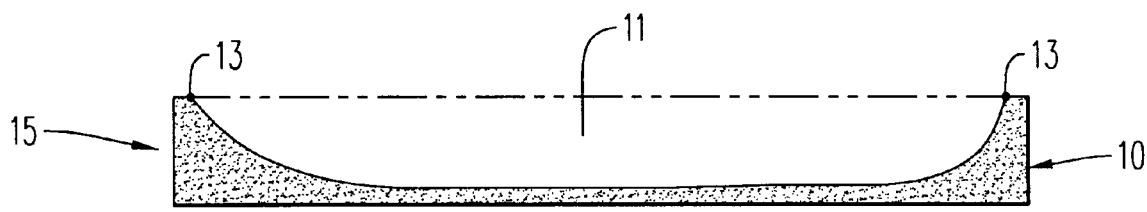
FIG. 6 is a sectional view of the impression block of FIG. 5 taken along lines 6—6.
Figure 7:
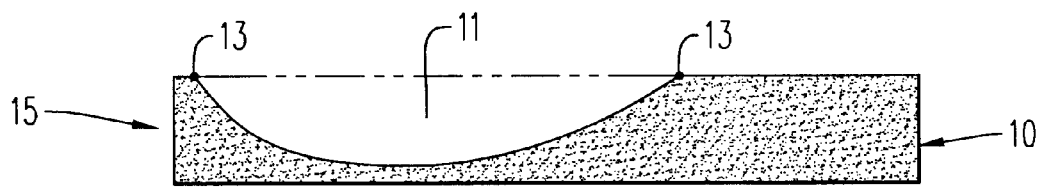
FIG. 7 is a sectional view of the impression block of FIG. 5 taken along lines 7—7.
Figure 8:
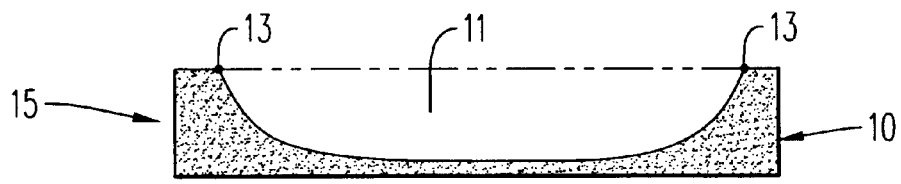
FIG. 8 is a sectional view of the impression block of FIG. 5 taken along lines 8—8.
Figure 6A:
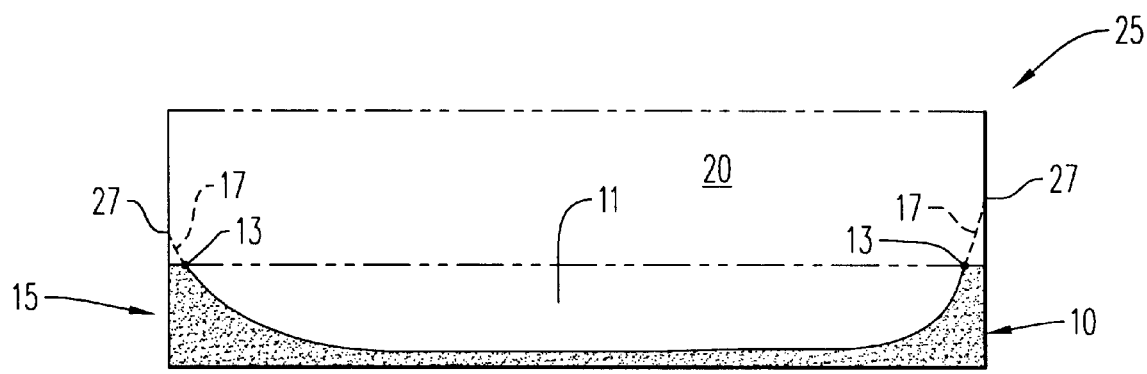
FIG. 6a is a comparison of the impression block of FIG. 6 and the insole blank.
Figure 7A:
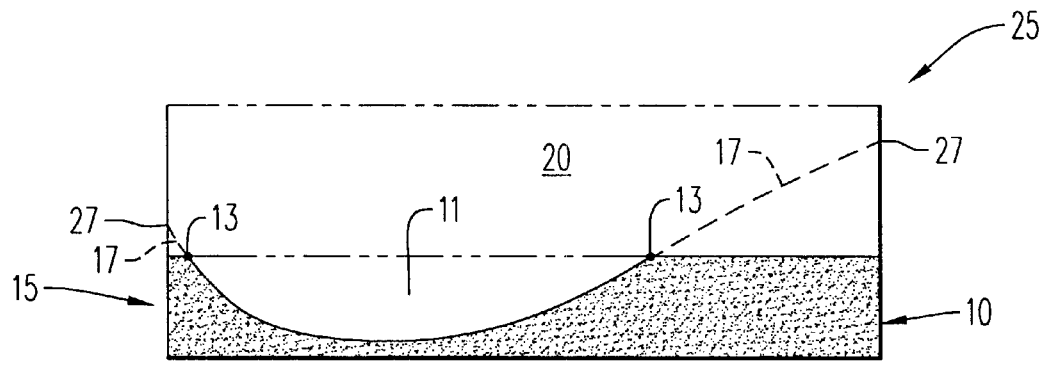
FIG. 7a is a comparison of the impression block of FIG. 7 and the insole blank.
Figure 8A:
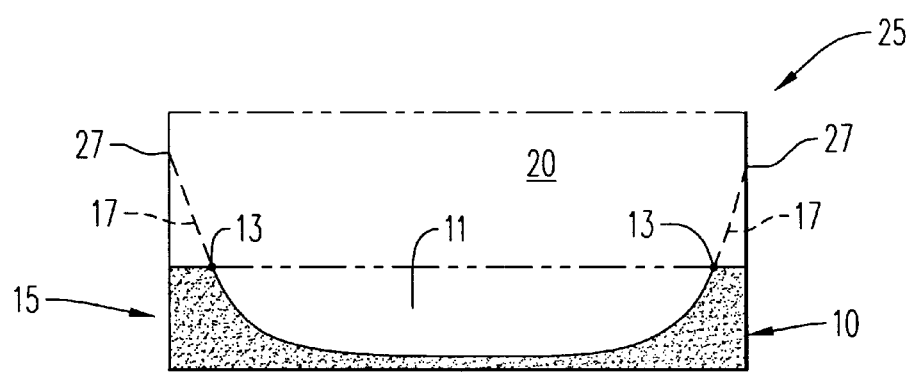
FIG. 8a is a comparison of the impression block of FIG. 8 and the insole blank.

By way of example, the formation of complete plantar contour 11' from partial plantar contour 11 is described by the tangential line method shown in FIGS. 6 through 8. In this method, each cross-section 15 is analyzed at points 13 where partial plantar contour 11 exits block 10. A tangent line 17 to partial plantar contour 11 at each point 13 is derived. Finally, the partial plantar contour 11 is continued along tangent line 17 to form complete plantar contour 11'. Thus, analysis of a plurality of cross sections 15 of block 10 having partial plantar contour 11 extrapolates complete plantar contour 11'.

While the present invention is described above using the tangential line method, other prior art numerical methods including, but not limited to linear interpolation, quadratic interpolation, Newton's Forward-Backward-Difference interpolation, Everett interpolation, Lagrange interpolation and the like, are considered within the scope of the present invention for forming complete plantar contour 11' from partial plantar contour 11.

Reduction in thickness 12 of block 10 provides numerous advantages over prior art blocks. For example, thickness 12 reduces shelf space requirements for block 10 at the point of sale, reduces packaging costs for block 10, reduces the amount of block 10 that it required, thus reducing manufacturing costs and shipping costs, as well as damage that may occur during shipping. In the instance where block 10 is directed for use at home by the user and then to be shipped to a location for manufacture of the insole, reduced shipping costs provides a significant advantage. Additionally, thickness 12 enables the foot of the user to completely deform or bottom out in block 10, which can provide a more accurate impression of the plantar contour.

In an alternate embodiment, the present invention not only extrapolates complete plantar contour 11', but also ensures that the complete plantar contour smoothly intersects the insole blank at a desired point. This requires a digitized model of, for example, the insole blank. The present invention is describe herein by example using types of insole blanks are commonly used to form custom insoles, namely die cut blanks 20 and molded blanks 30. However, other types of blanks, such as, but not limited to, sheets of blank material are considered within the scope of the present invention.

Die cut blank 20 is shown in FIGS. 9 through 12. A plurality of die cut blanks 20 are cut from a single sheet of insole forming material into the desired shape. For example, FIG. 9a shows die cut blank 20 in the form of a left foot insole. However, die cutting allows die cut blank 20 to be cut into other shapes, such as a right foot insole or a universal insole. Shown in FIG. 9b, die cut blank 20 has a constant thickness 22 across its length 23. Thickness 22 of die cut blank 20 is typically between about 30 mm to about 35 mm.

Figure 9A:
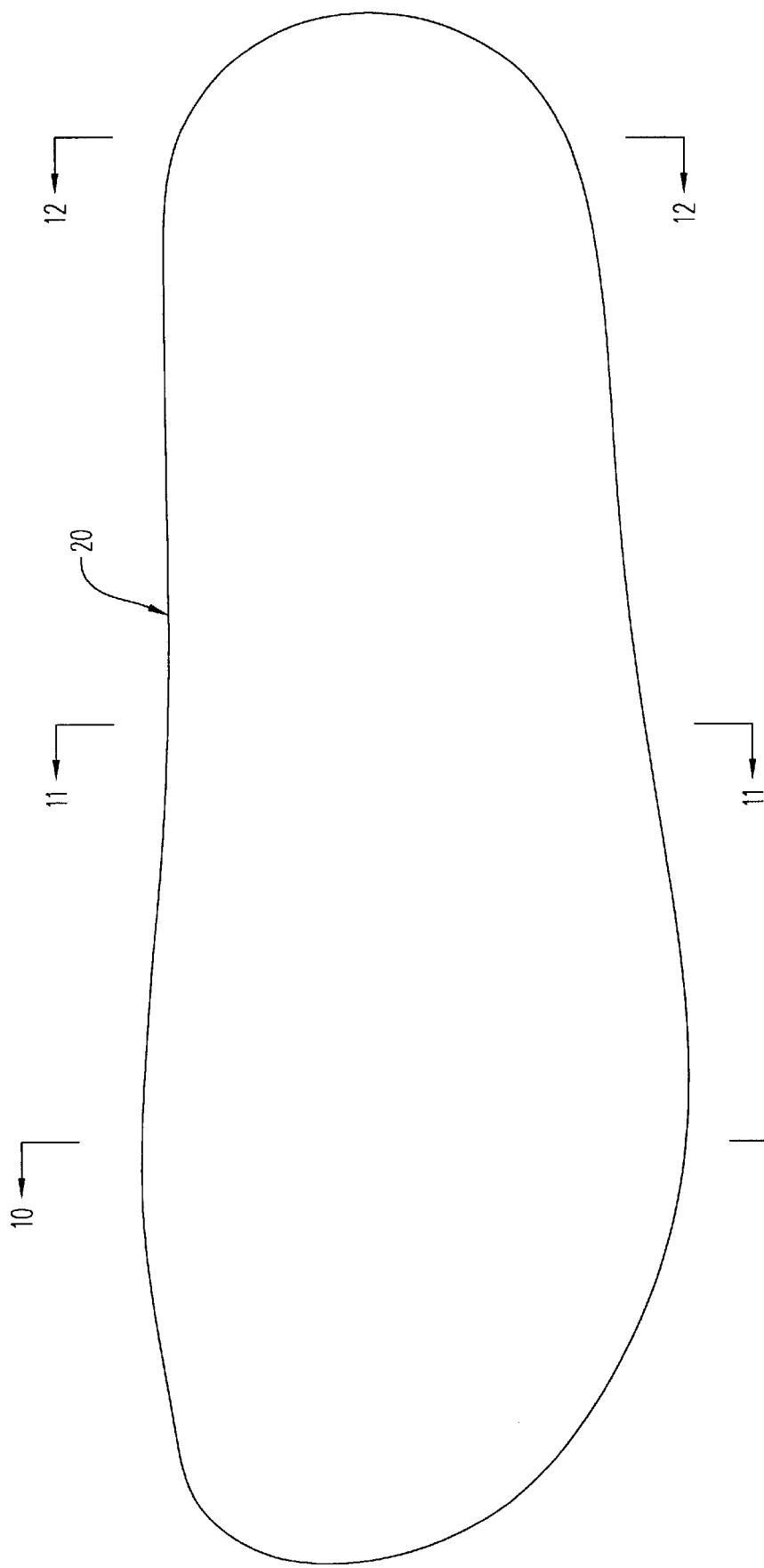
FIG. 9a is a top view of a die cut blank for a custom insole.
Figure 9B:
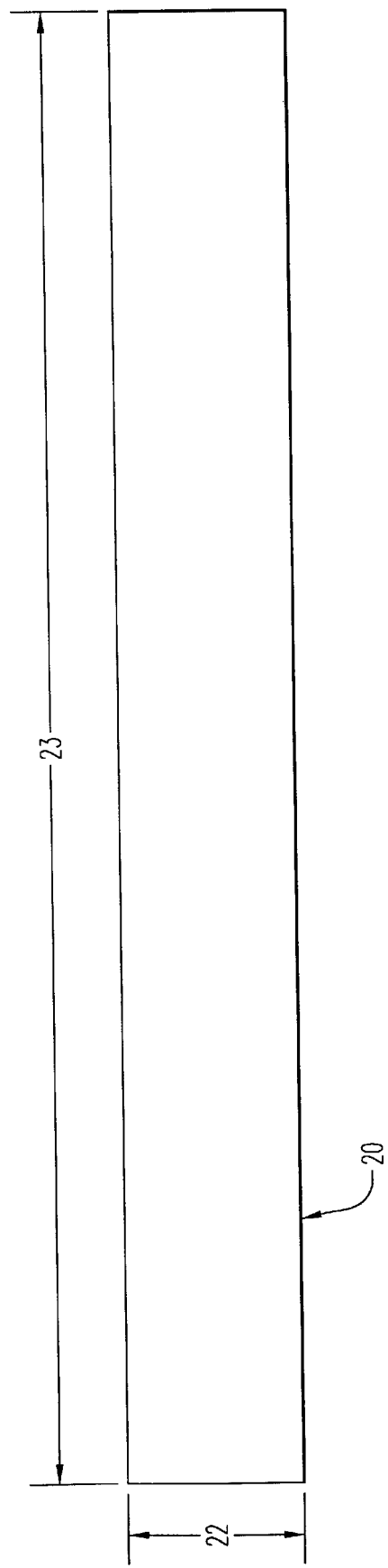
Figure 10:
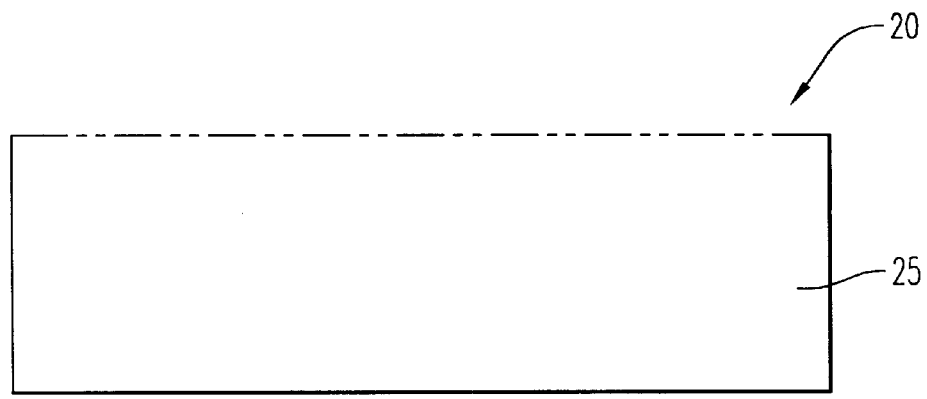
FIG. 10 is a cross section of the die cut blank of FIG. 9a taken along lines 10—10.
Figure 11:
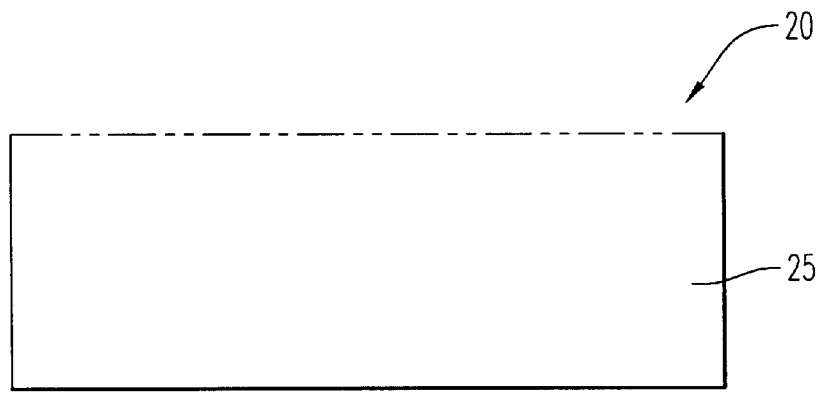
FIG. 11 is a cross section of the die cut blank of FIG. 9a taken along lines 11—11.
Figure 12:
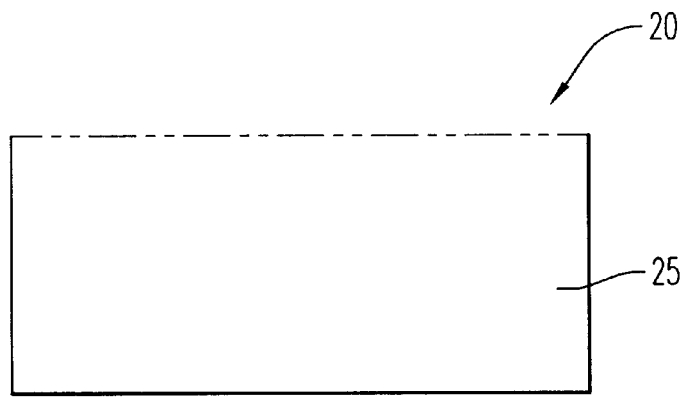
FIG. 12 is a cross section of the die cut blank of FIG. 9a taken along lines 12—12.

In order to ensure that the complete plantar contour smoothly intersects the insole blank, periodic cross-sections of the blank that correspond to cross-sections 15 of partial plantar contour 11 are generated. For example, a plurality of cross sections 25 shown in FIGS. 10 through 12 formed along lines 10—10 through 12—12 of FIG. 9a are generated of blank 20. Shown in FIGS. 6a through 8a, cross section 15 of complete plantar contour 11' is compared to each cross section 25 of blank 20. The present invention smoothes intersection 27 of the complete plantar contour and blank 20.

In an alternate embodiment, the height of the sole of the shoe that the custom insole is to be placed is the desired point used to define intersection 27. This requires a digitized model of, for example, the sole of the shoe that the custom insole is to be placed. In this embodiment, the point where each cross section 15 of complete plantar contour 11' crosses the cross section of the sole of the shoe forms the intersection 27 of the blank and the completed plantar contour 11'. In the instance of low profile insole supports, smoothing will be required to fit them into higher blanks if they are used.

Intersection 27 is smoothable by any number of smoothing methods such as, but not limited to, a radius fillet, bspline interpolation, and the like.

Figure 13:
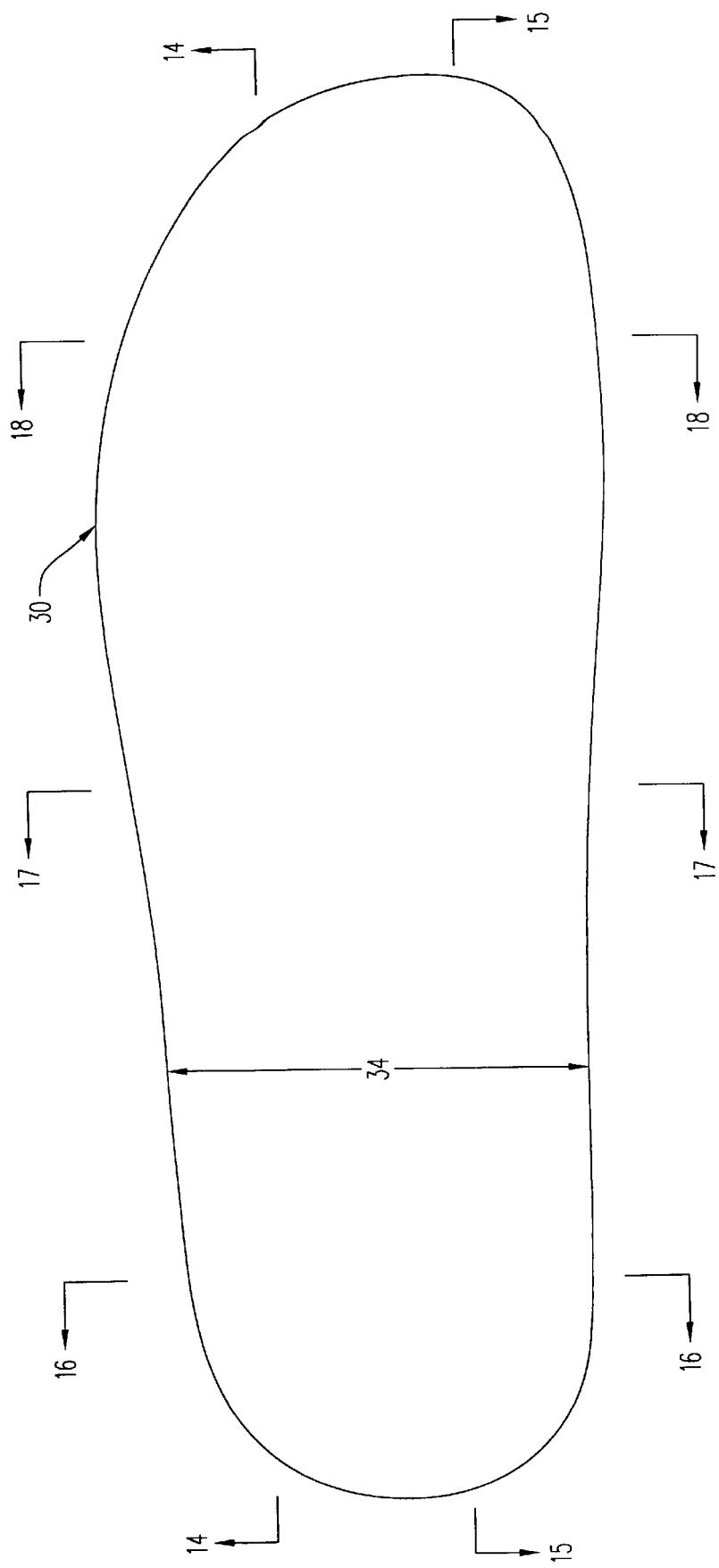
FIG. 13 is a top view of a molded blank for a custom insole.
Figure 15:
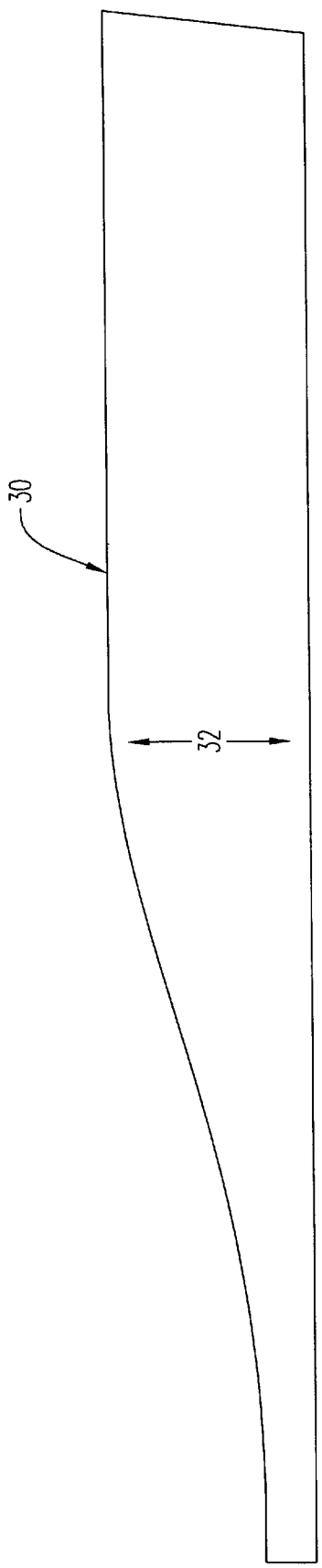
FIG. 15 is a cross section of the molded cut blank of FIG. 13 taken along lines 15—15.
Figure 14:
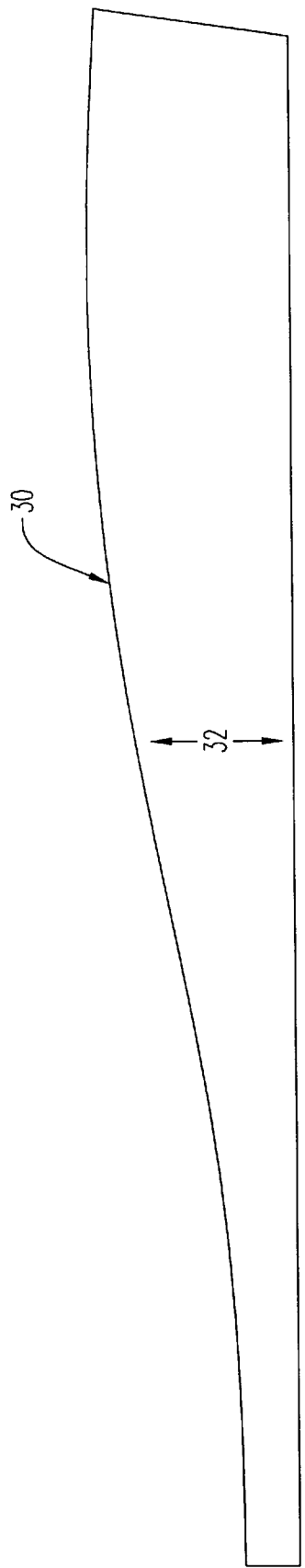
FIG. 14 is a cross section of the molded cut blank of FIG. 13 taken along lines 14—14.
Figure 18:
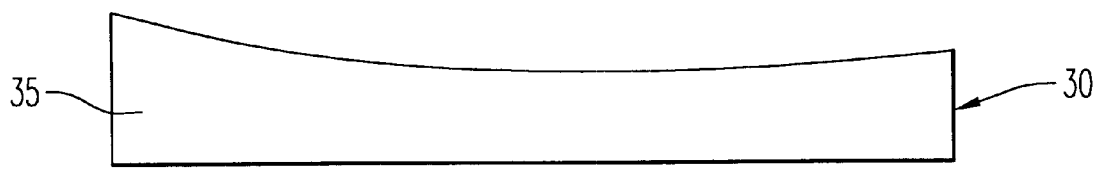
FIG. 18 is a cross section of the molded blank of FIG. 13 taken along lines 18—18.
Figure 17:
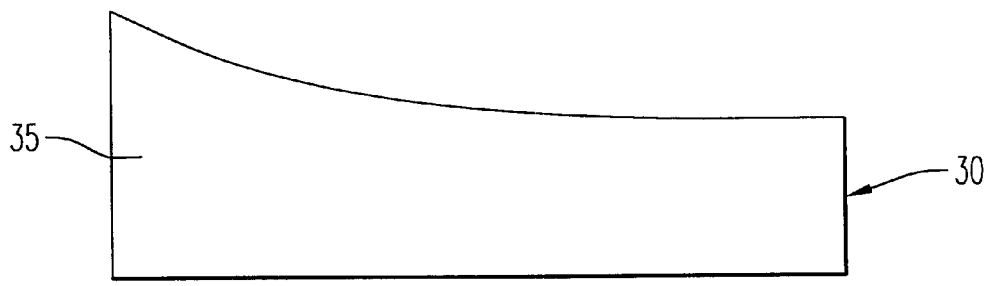
FIG. 17 is a cross section of the molded blank of FIG. 13 taken along lines 17—17.
Figure 16:
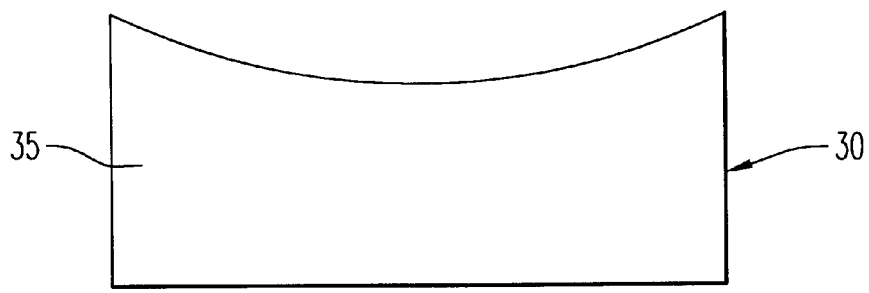
FIG. 16 is a cross section of the molded blank of FIG. 13 taken along lines 16—16.
Figure 19:
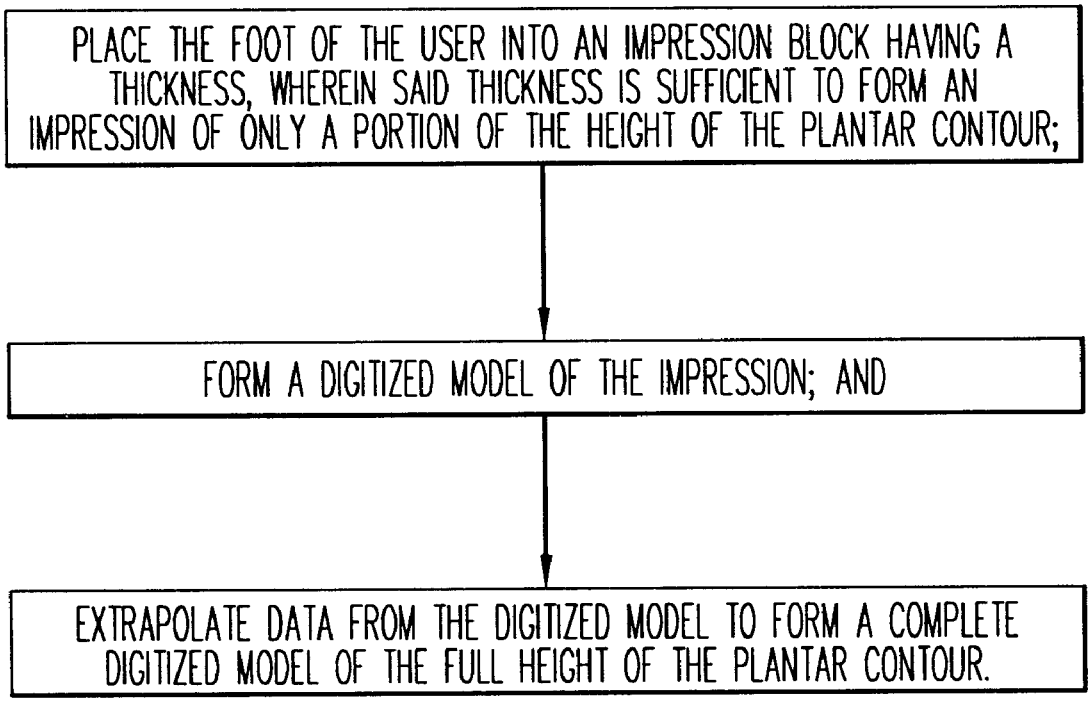
FIG. 19 is a block diagram showing a method of forming a complete digitized model of the height of a plantar contour of a foot of a user according to the present invention.

Molded blank 30 is shown in FIGS. 13 through 16. Each molded blank is molded to have a predetermined shape and profile. For example, FIG. 13 shows molded blank 30 in the form of a left foot insole. However, molding allows molded blank 30 to be formed into other shapes, such as a right foot insole or a universal insole. Shown in FIGS. 13 through 15, molding molded blank 30 allows for a varying thickness 32 and width 34 across its length 33. Thickness 32 of molded blank 30 typically ranges between a minimum of about 10 mm to maximum of about 35 mm, more preferably between 15 mm to 20 mm. For example, FIGS. 16 through 18 show various different cross-sections 35 taken along lines 16—16 through 18—18, respectively, of FIG. 13.

Similar to the discussion above with respect to die cut banks 20, cross sections 35 of molded blank 30 that correspond to cross sections 15 of partial plantar contour 11 are generated by the scanning system. The scanning system compares each cross section 15 of complete plantar contour 11' to cross section 35 of molded blank 30 and smoothes the intersection of the complete plantar contour and the molded blank. With extrapolation, the foot contour can be cut into insoles with approximately 10 mm in the arch and heal cups, and thereby provide the smoothing with the edges of the blanks.

Figure 20A:
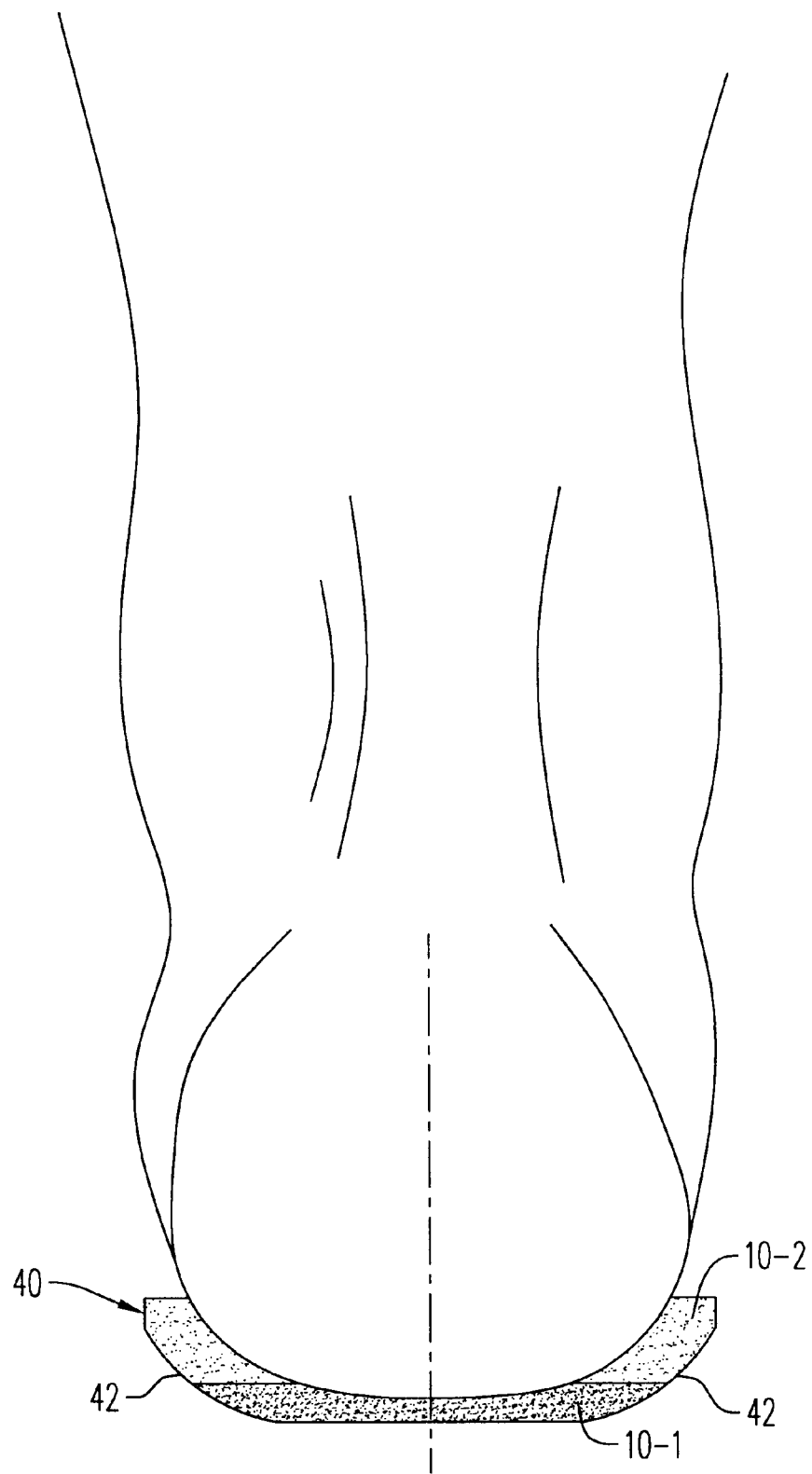
FIG. 20a is a rear view of a foot placed into a dual density embodiment of the present invention.
Figure 20B:
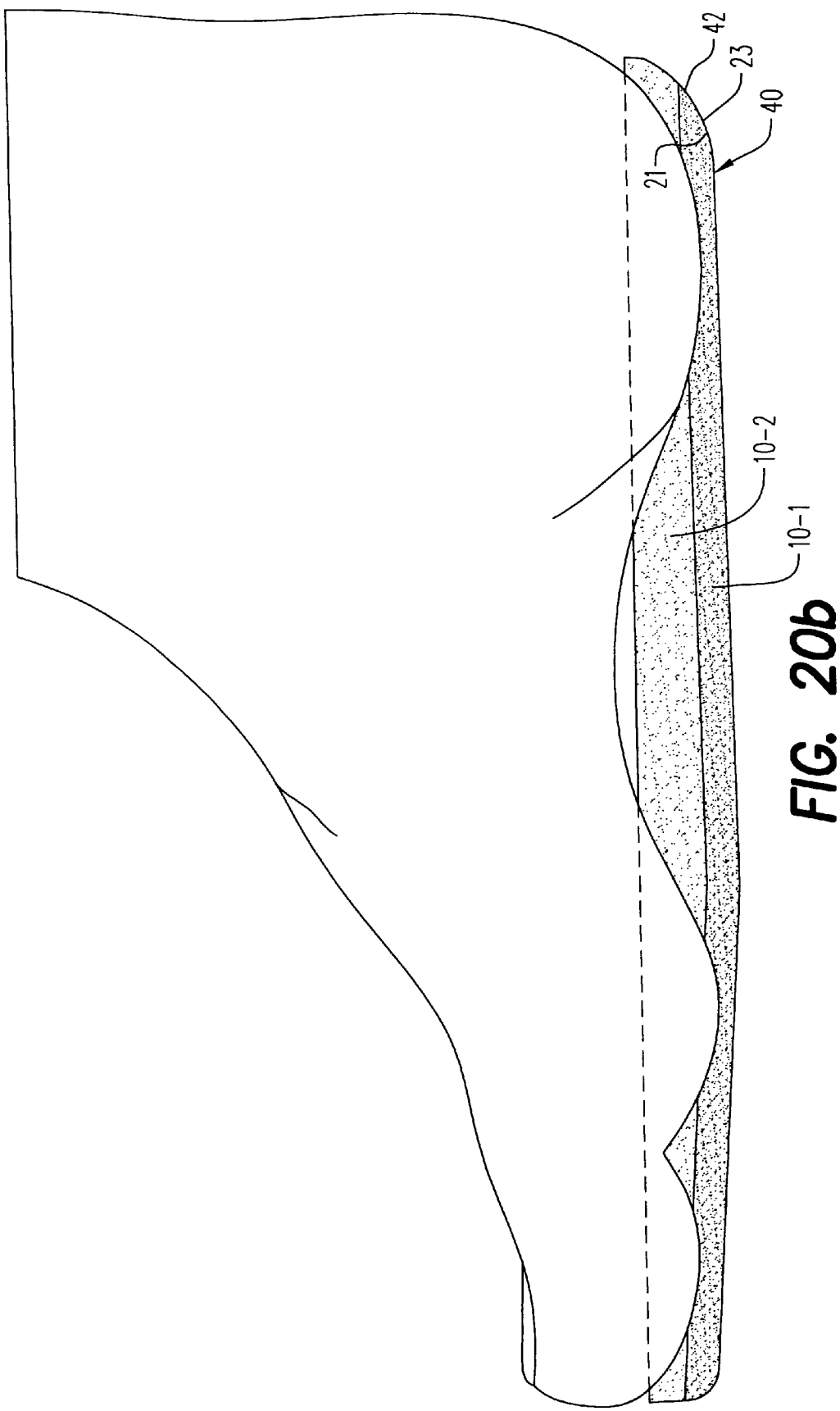

In an alternate embodiment shown in FIGS. 20a and 20b, block 10 is provided with a plurality of regions having different densities. By way of example, block 10 includes a region 10-1 having a first density and a region 10-2 having a second lower density. Thus, block 10 is adapted to manipulate the foot of the user during the forming of the impression. For instance, region 10-1, being of higher density, ensures improved or better support for the heal and other plantar surfaces. In a preferred embodiment, region 10-1 has a density of 5 psi and region 10-2 has density of 3 psi. In this embodiment, the higher density of region 10-1 ensures that the foot is properly centered within the lower density region 10-2.

Also shown in FIGS. 20a and 20b, the inside 21 wall and outside 23 wall of carrier 40 are both shaped having a radius 42 between the sidewall and the bottom wall. Radius 42 is adapted to ensure that the heel of the user is properly centered within block 10. Thus, radius 42 further improves the accuracy of the measurement of a person's foot by more closely approximating the position and shape their foot will assume when properly centered.

Figure 21:
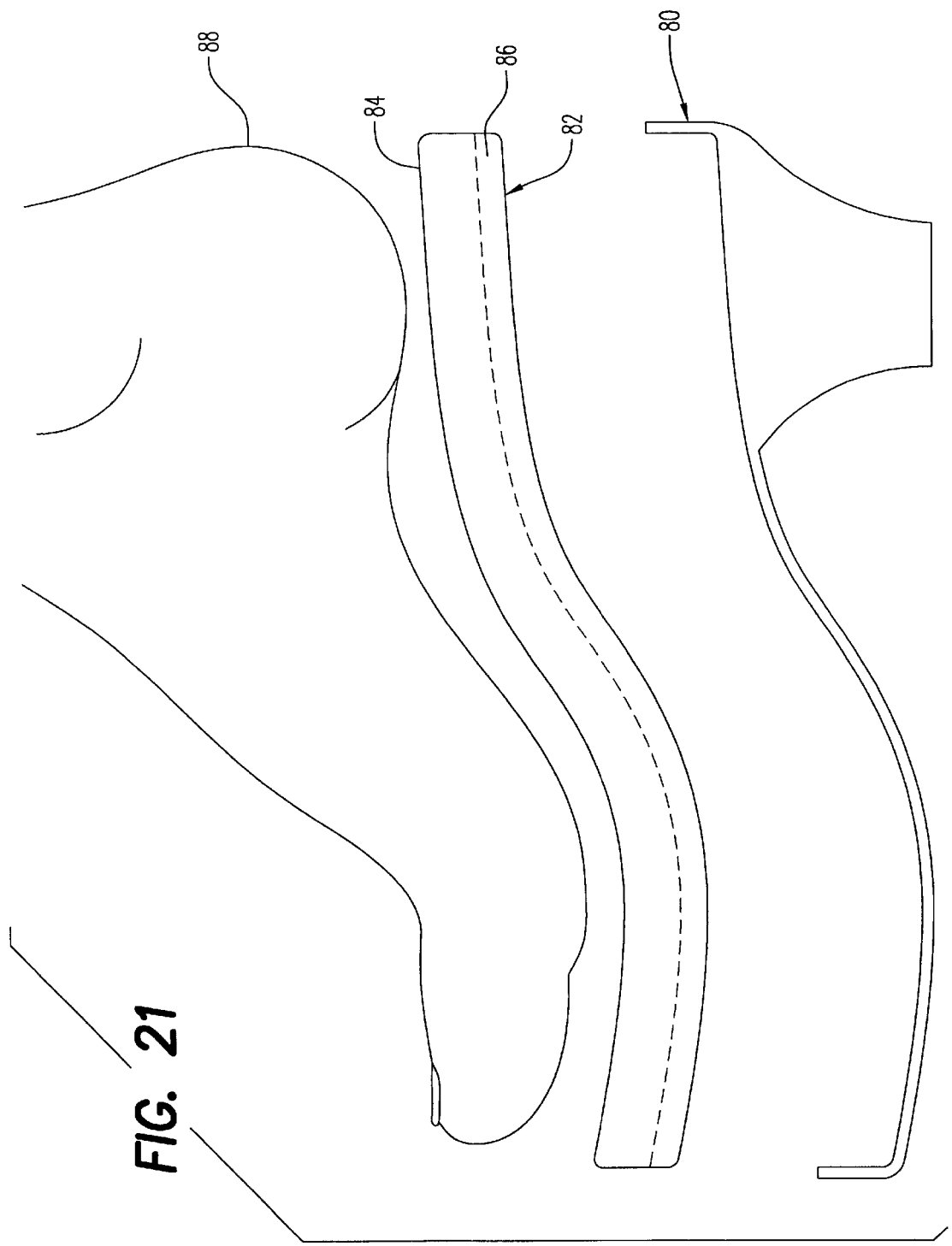
FIG. 21 is a schematic exploded side view of a partial women's heeled shoe, a dual density cartridge according to the present invention and a foot.
Figure 22:
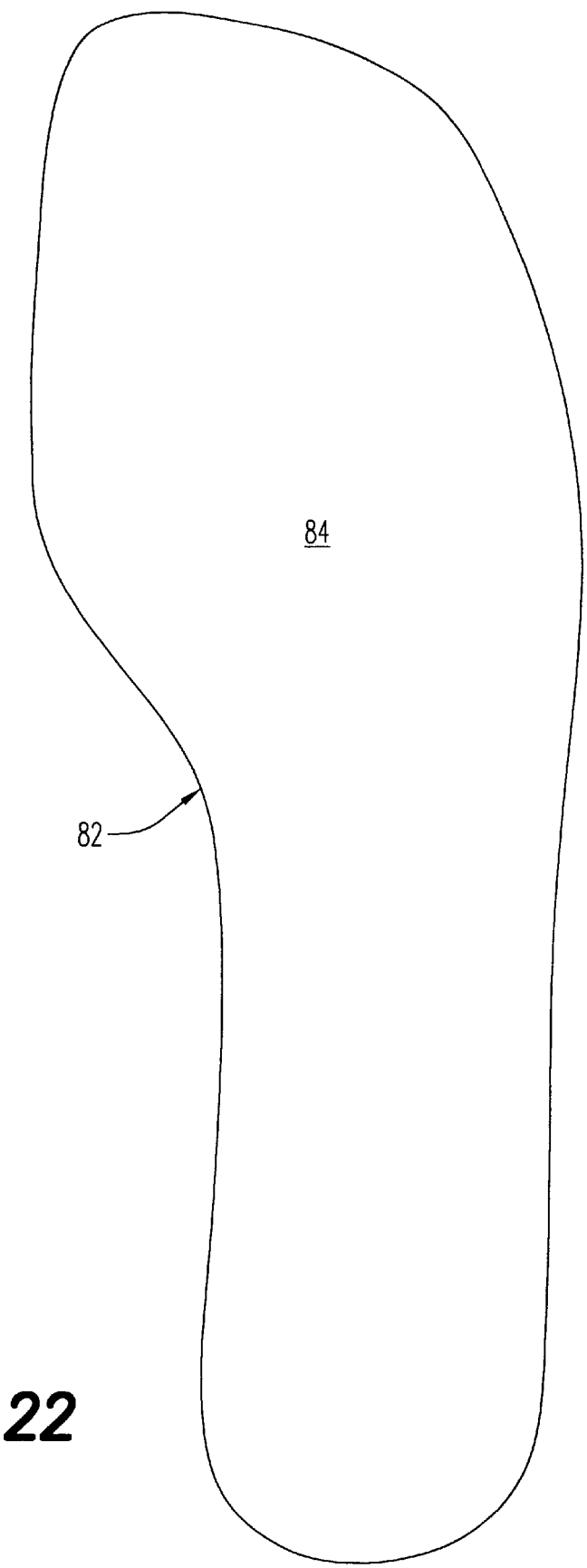
FIG. 22 is a top view of the dual density cartridge of FIG. 21.
Figure 23:
FIG. 23 is a schematic side view of a foot positioned above a carrier filled with dual density foam according to the present invention.
Figure 24:
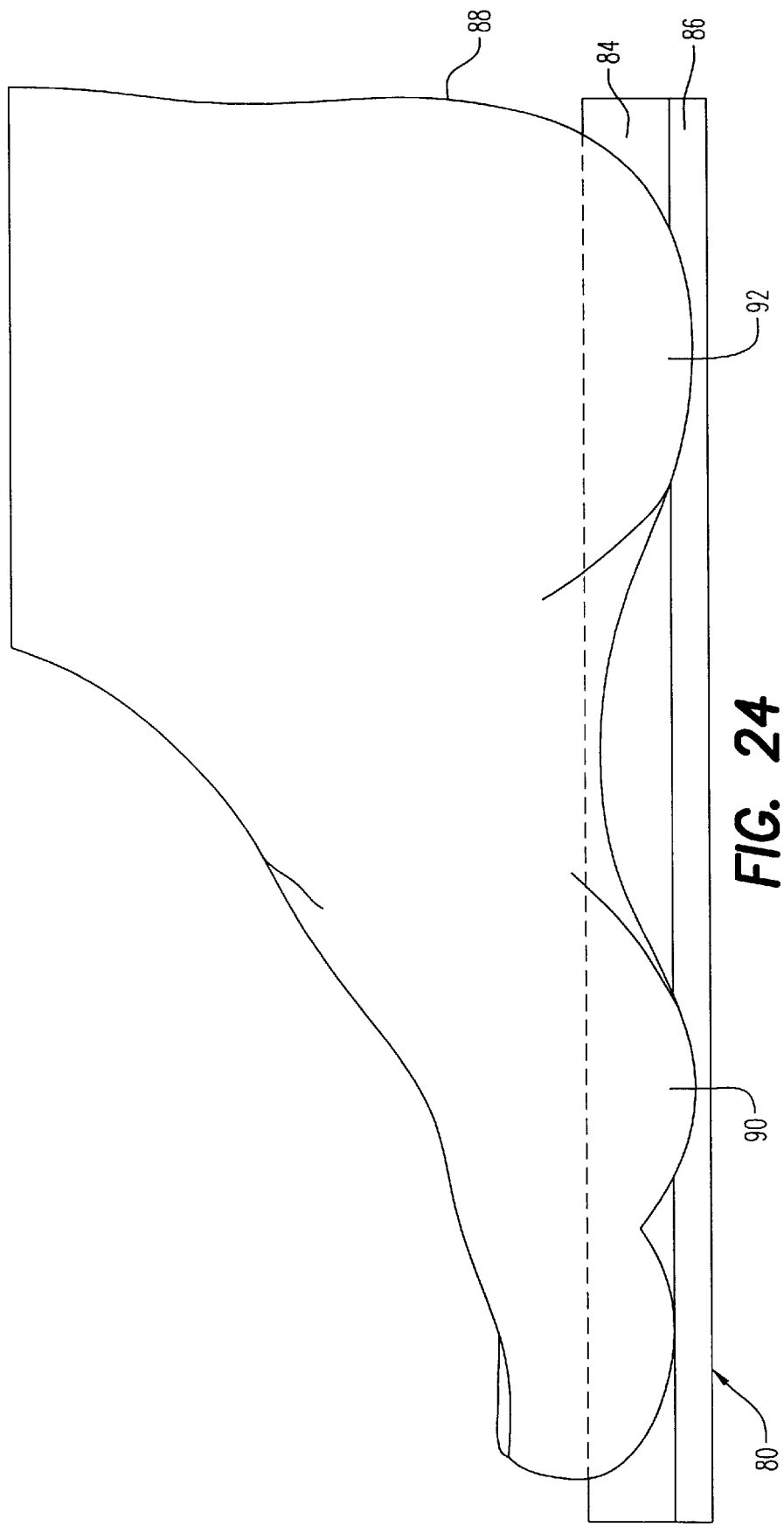
FIG. 24 is a schematic side view of a foot with pressure being applied thereto such that the dual density foam according to the present invention is depressed downward such that both the ball and heel of the foot are compressed into the higher density foam.
Figure 25A:
FIG. 25a is a schematic side view of a foot positioned above a shorter three quarters sized dual density foam impression cartridge according to another embodiment of the present invention.
Figure 25B:
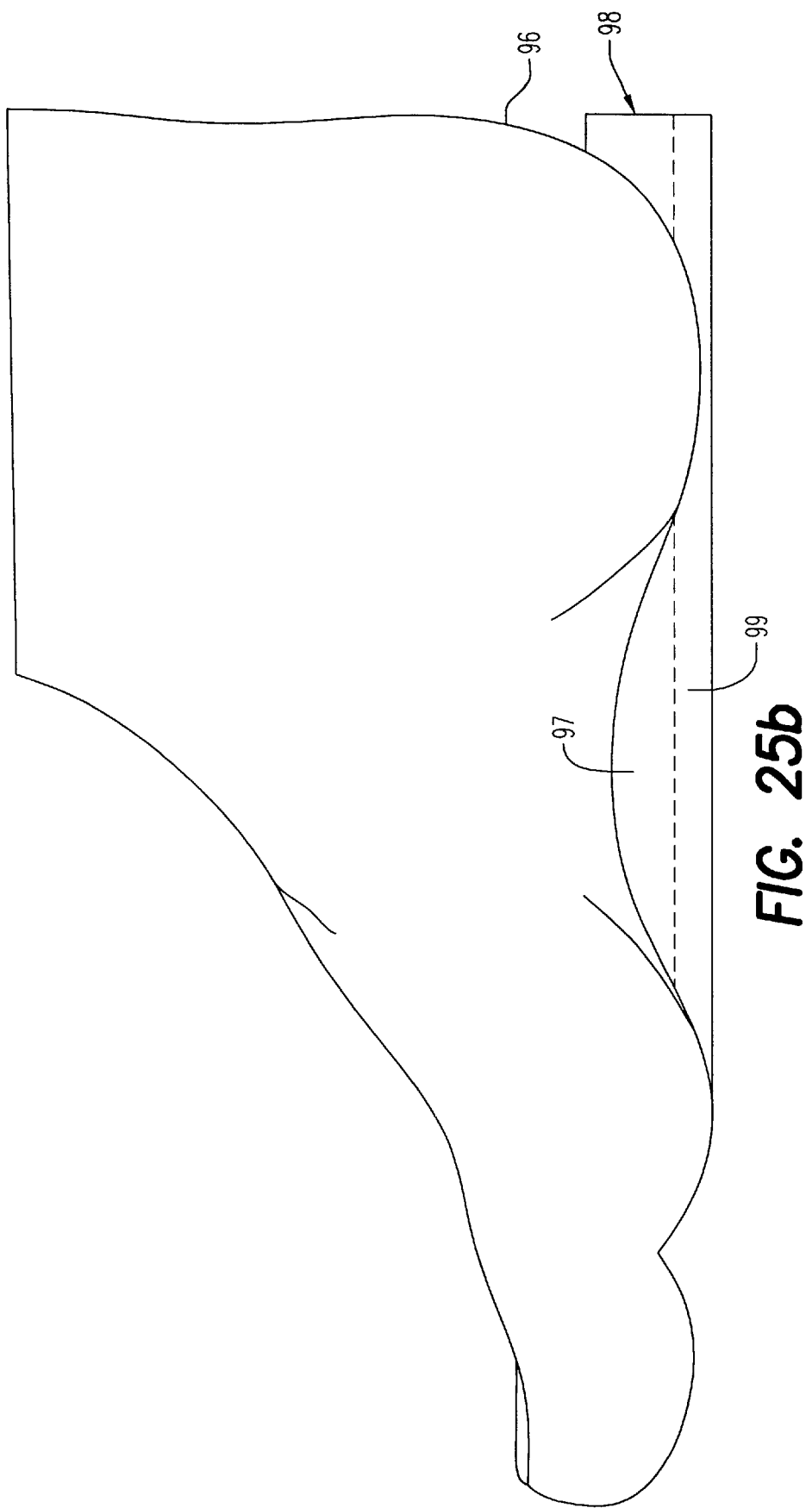
FIG. 25b is a schematic side view of a foot with pressure being applied thereto such that the dual density foam impression cartridge of FIG. 25a is depressed downward such that only an impression of the heel and the arch are left.
Figure 26B:
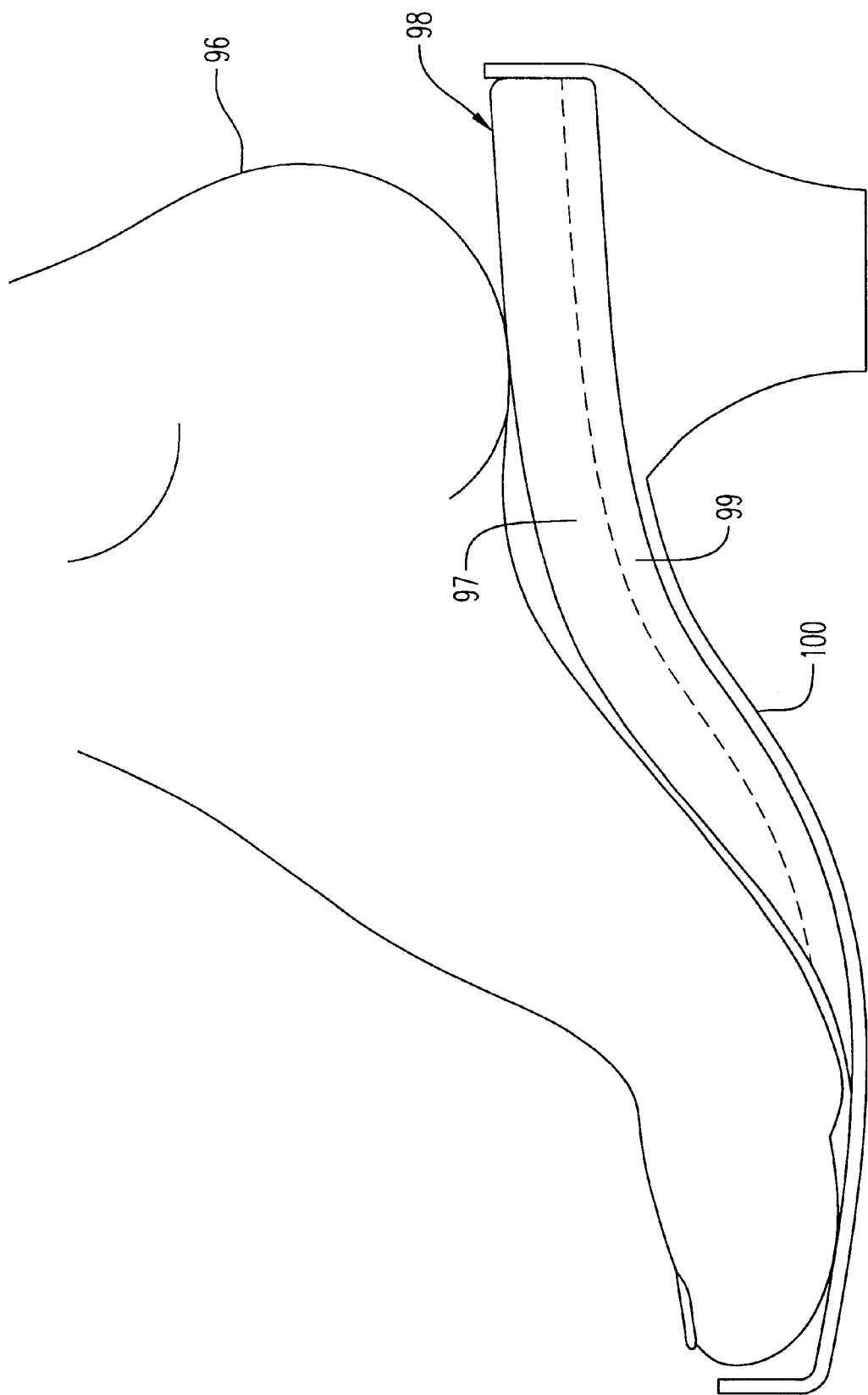
FIG. 26b is a schematic side view of a foot positioned above a shorter three quarters sized dual density foam impression cartridge disposed within a partial women's heeled shoe.
Figure 26C:
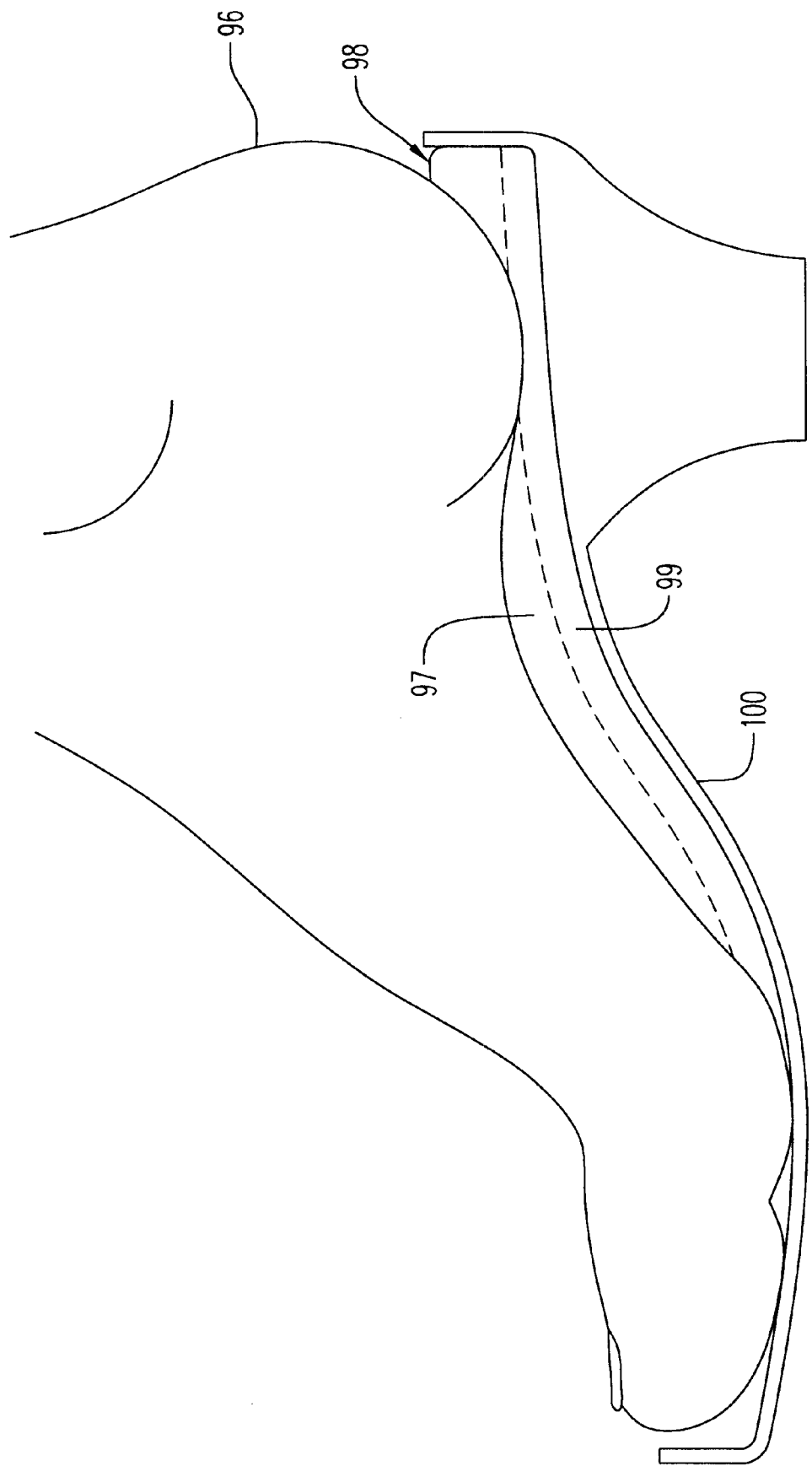
FIG. 26c is a schematic side view of a foot with pressure being applied thereto such that the dual density foam impression cartridge of FIG. 26b is depressed downward such that only an impression of the heel and the arch are left.
Figure 27:
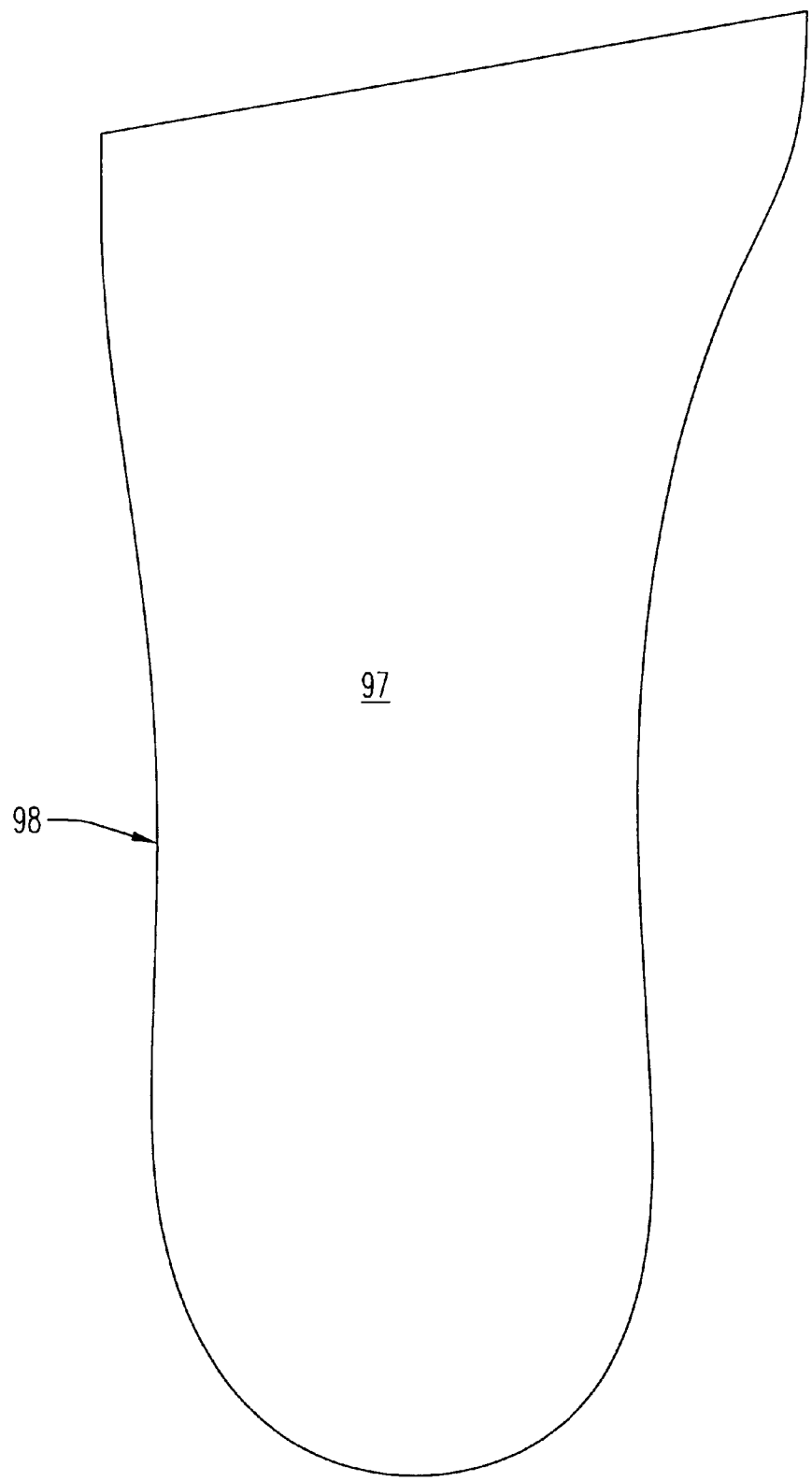
FIG. 27 is a top planar view of a three quarters sized dual density foam impression cartridge according to the present invention.

FIG. 21 is a schematic exploded side view of a partial women's heeled shoe 80, a dual density cartridge 82 comprising a first lower density layer 84 and second higher density layer 86, and foot 88. FIG. 22 is a top view of dual density cartridge 82. FIG. 23 is a schematic side view of a foot 88 positioned above a carrier filled with dual density foam 82 prior to making a impression. FIG. 24 is a schematic side view of a foot 88 with pressure being applied thereto such that the dual density foam 82 is depressed downward such that both the ball 90 and heel 92 of foot 88 are compressed into higher density foam layer 86.

FIGS. 25a through 27 depict another embodiment according to the present invention wherein a foot 96 applies pressure to a shorter or partial (e.g., three quarters sized) dual density foam impression cartridge 98 comprising a first lower density layer 97 and second higher density layer 99. FIGS. 26a–26c demonstrate cartridge 98 deposed within at least a portion of a shoe 100, wherein shoe 100 acts as a carrier for cartridge 98.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. An apparatus for measuring a plantar contour of a foot of a user, comprising:
   a carrier; and
   an impression block in said carrier, wherein said impression block has at least one indentation formed therein to aid the user in aligning the foot with respect to said impression block.

2. The apparatus of claim 1, wherein the plantar contour has a height of about less than 20 millimeters and said impression block has a thickness sufficient to form an impression of at least a portion of said height of the plantar contour, wherein said at least a portion is equal to less than half of said height of the plantar contour.

3. The apparatus of claim 1, the plantar contour having a height, and said impression block having a first end portion having a thickness in the range from about 8 mm to about 10 mm and a second end portion having a thickness in the range from about 10 mm to about 15 mm., wherein said first and second end portions are disposed opposite to one another.

4. The apparatus of claim 1, the plantar contour having a height, and wherein said carrier is symmetrical about its longitudinal axis such that said impression block is adapted to measure the plantar contour of either foot of the user.

5. The apparatus of claim 1, the plantar contour having a height, wherein said impression block includes a plurality of regions having different densities.

6. The apparatus of claim 5, wherein said plurality of regions having different densities have a density in a range from about 0.5 to 25 psi.

7. The apparatus of claim 6, wherein said density is in a range from about 8 to 15 psi.

8. A method for forming a complete digitized model of the height of a plantar contour of a foot of a user, wherein the plantar contour has a height, the method comprising:
  placing the foot of the user into an impression block having a thickness, wherein said thickness is sufficient to form an impression of at least a portion of the height of the plantar contour;
  forming a digitized model of said impression; and
  extrapolating data from said digitized model of said impression to form either a complete or partial digitized model of the full or partial height of the plantar contour, respectively, wherein said extrapolating data comprises:
    forming a plurality of cross sections of said digitized model of said impression;
    analyzing each cross section at a point where said impression exits said impression block;
    deriving a tangent line to said impression at each said point; and
    forming said complete digitized model using each said tangent line.

9. The method of claim 8, wherein said digitized model of said impression is formed by the group consisting of optically scanning said impression and scanning a positive model of said impression.

10. A method for forming a complete digitized model of the height of a plantar contour of a foot of a user, wherein the plantar contour has a height, the method comprising:
  placing the foot of the user into an impression block having a thickness, wherein said thickness is sufficient to form an impression of at least a portion of the height of the plantar contour;
  forming a digitized model of said impression; and
  extrapolating data from said digitized model of said impression to form either a complete or partial digitized model of the full or partial height of the plantar contour, respectively, wherein said extrapolating data comprises:
    forming said complete digitized model using a numerical method selected from the group consisting of linear interpolation, quadratic interpolation, Newton's Forward-Backward-Difference interpolation, Everett interpolation, and Lagrange interpolation.

11. The method of claim 10, wherein said digitized model of said impression is formed by the group consisting of optically scanning said impression and scanning a positive model of said impression.

12. An apparatus for measuring a plantar contour of a foot of a user, the plantar contour having a height, the apparatus comprising:
  an impression block having a plurality of regions having different densities.

13. The apparatus of claim 12, wherein said impression block has a guide formed therein to aid the user in aligning the foot with respect to said impression block.

14. The apparatus of claim 13, wherein said guide comprises an indentation formed within said impression block.

15. The apparatus of claim 12, wherein said impression block is expanded phenolic material.

16. The apparatus of claim 12, further comprising a carrier having said impression block disposed therein, and wherein said carrier is symmetrical about its longitudinal axis such that said impression block is adapted to measure the plantar contour of either foot of the user.

17. The apparatus of claim 12, wherein said impression block is contained within a compliant medium.

18. An apparatus for measuring a plantar contour of a foot of a user, the plantar contour having a height, the apparatus comprising:
  an impression block having at least a first layer and a second layer, wherein said first layer is disposed on top of said second layer, and wherein said first layer is of a lesser density than said second layer.

19. The apparatus of claim 18, wherein said first layer has a density in the range between about 0.5 to 5 psi and said second layer has a density in the range between about 5 to 25 psi.

20. The apparatus of claim 19, wherein said first layer has a density in the range between about 2 to 3 psi.

21. The apparatus of claim 19, wherein said second layer has a density in the range between about 5 to 10 psi.

22. The apparatus of claim 18, further comprising a third layer, wherein said second layer is disposed between said first layer and said third layer, and wherein said third layer has a density greater than either said first or second layers.

23. The apparatus of claim 22, wherein said third layer has a density in the range between about 5 to 25 psi.

24. The apparatus of claim 23, wherein said third layer has a density in the range between about 8 to 15 psi.

25. An apparatus for measuring a plantar contour of a foot, comprising:
  a permanently deformable impression block; and
  a carrier, wherein said impression block and carrier form an integral container, and the plantar contour has a height of about less than 20 millimeters and said impression block has a thickness sufficient to form an impression of at least a portion of said height of the plantar contour, wherein said portion is equal to less than half of said height of the plantar contour.

26. An apparatus for measuring a plantar contour of a foot, comprising:
  a permanently deformable impression block; and
  a carrier, wherein the plantar contour has a height of about less than 20 millimeters and said impression block has a thickness sufficient to form an impression of at least a portion of said height of the plantar contour, wherein said portion is equal to less than half of said height of the plantar contour.

27. An apparatus for measuring a plantar contour of a foot, comprising:
  a permanently deformable impression block; and
  a carrier, wherein said impression block and carrier form an integral container.

* * * * *